(12) United States Patent
Tang et al.

(10) Patent No.: US 9,341,736 B2
(45) Date of Patent: May 17, 2016

(54) GOODS INSPECTION APPARATUS USING DISTRIBUTED X-RAY SOURCE

(71) Applicants: NUCTECH COMPANY LIMITED, Beijing (CN); TSINGHUA UNIVERSITY, Beijing (CN)

(72) Inventors: Huaping Tang, Beijing (CN); Yuanjing Li, Beijing (CN); Ziran Zhao, Beijing (CN); Yaohong Liu, Beijing (CN); Zhanfeng Qin, Beijing (CN); Jinyu Zhang, Beijing (CN); Hu Tang, Beijing (CN)

(73) Assignees: TSINGHUA UNIVERSITY, Beijing (CN); NUCTECH COMPANY LIMITED, Beijing (CN)

( * ) Notice: Subject to any disclaimer, the term of this patent is extended or adjusted under 35 U.S.C. 154(b) by 263 days.

(21) Appl. No.: 14/134,845

(22) Filed: Dec. 19, 2013

(65) Prior Publication Data

US 2014/0185754 A1    Jul. 3, 2014

(30) Foreign Application Priority Data

Dec. 31, 2012   (CN) ............................ 2012 1 0588867

(51) Int. Cl.
  *G01N 23/04*    (2006.01)
  *G01V 5/00*     (2006.01)
(52) U.S. Cl.
  CPC .................................... *G01V 5/0016* (2013.01)

(58) Field of Classification Search
  CPC .......... G01V 5/0016; G01V 5/08; G01N 23/04
  USPC ............................................................. 378/57
  See application file for complete search history.

(56) References Cited

U.S. PATENT DOCUMENTS

| | | | |
|---|---|---|---|
| 7,177,391 B2 | 2/2007 | Chapin et al. | |
| 2010/0277312 A1* | 11/2010 | Edic ........................ | G01V 5/005 340/540 |
| 2011/0286581 A1 | 11/2011 | Sprenger et al. | |

FOREIGN PATENT DOCUMENTS

| | | |
|---|---|---|
| CN | 1658796 | 8/2005 |
| CN | 1841053 A | 10/2006 |
| CN | 100591277 | 2/2010 |
| CN | 202041481 U | 11/2011 |
| CN | 203341743 | 12/2013 |
| JP | 6-261895 | 9/1994 |
| JP | 2005-276760 A | 10/2005 |
| WO | 2009/115982 | 9/2009 |

OTHER PUBLICATIONS

Search Report dated Mar. 27, 2014 from PCT/CN2013/001575.

* cited by examiner

*Primary Examiner* — Courtney Thomas
(74) *Attorney, Agent, or Firm* — Casimir Jones, SC (57) ABSTRACT

This invention relates to an X-ray goods inspection apparatus, and in particular to a goods inspection apparatus using distributed X-ray source.

8 Claims, 4 Drawing Sheets

GOODS INSPECTION APPARATUS USING DISTRIBUTED X-RAY SOURCE

CROSS-REFERENCE TO RELATED APPLICATION

The present application claims priority to pending Chinese Patent Application No. CN201210588867.4, filed Dec. 31, 2012, the contents of which are incorporated by reference its entirety.

TECHNICAL FIELD

This invention relates to an X-ray goods inspection apparatus, and in particular to a goods inspection apparatus using distributed X-ray source. This invention provides a goods inspection apparatus using distributed X-ray source, comprising: a frame; a goods passage; a goods conveyor; a distributed X-ray source for producing X-ray at different positions successively within each working cycle; a detector array for receiving the X-ray from the distributed X-ray source and outputting signals indicating the strength of the X-ray; an electronics system for receiving signals from the detectors, converting the signals into digital ones, and forming a data packet with the position numbers of corresponding detectors, outputting a sequence of data packets formed by the position numbers and signals from the plurality of detectors of the detector array; an image processing system for receiving the output from the electronics system, processing the position numbers of detectors and the corresponding signals indicating the strength of X-ray, constructing to form an image of the object under inspection; a ray source power supply for providing power to the distributed X-ray source; and a control system for exercising logical control over the respective parts to enable the respective sub-systems to work in coordination.

BACKGROUND ART

An X-ray goods inspection apparatus is an instrument that uses the X-ray imaging principle to have such objects as industrial products, baggage and human body X-rayed to acquire information about the fine structure of the object under inspection, thereby achieving such purposes as defect determining, dangerous goods checking, medical diagnosis and so on. X-ray goods inspection apparatus is widely applied in such fields as industrial nondestructive examination, security check, medical diagnosis and treatment. At the early stage, said apparatus was a planer X-ray imaging device of film, but now is the advanced digital 3D imaging device of high definition and multi-angle of view, e.g., computed tomography (CT), capable of acquiring 3D graphics or section images of high definition, being an advanced high-end application.

In a CT device (such as industrial defect detection CT, baggage inspection CT, medical diagnosis CT and so on), it is usual to put the X-ray source at one side of the object under inspection and a detector for receiving ray at the other side. When X-ray passes through an object, its strength varies with such information as the thickness and density of the object. The strength of X-ay received by the detector includes the structural information of one angle of view of the object under inspection. If the X-ray source and detector rotate around the object under inspection, we can acquire the structural information of different angle of view. Restructuring said information by a computer system and software algorithm can obtain a 3D image of the object under inspection. At present, the CT device is securing the X-ray source and detector to a circular slip ring surrounding the object under inspection. Every round of movement in work can get an image of a section of one thickness of the object under inspection, which is called a section. The object under inspection then moves along the direction of thickness to obtain a series of sections, which put together is just a fine 3D structure of the object under inspection. Therefore, for an existing CT device, in order to acquire information of different angle of view, it has to change the position of the X-ray source, so the X-ray source and detector need to move on the slip ring. To step up the inspection, the moving speed of the X-ray source and detector is often very fast. Due to the high speed movement on the slip ring, the overall reliability and stability of the device are reduced. Besides, as hindered by the moving speed, the CT inspection speed is also limited. Although the newest generation of CT in recent years mounts the detector in a circumferential manner such that the detector does not have to move, the X-ray source still has to move on the slip ring. Besides, multiple rows of detectors may be mounted so that a plurality of section images can be obtained every round the X-ray source moves, thereby increasing the CT inspection speed, but this does not solve the problem of complex structure and low inspection speed resulted from the movement on the slip ring fundamentally.

Besides, Nuctech Company Limited manufactures a type of light source apparatus that generates distributed X-ray, exhibiting a distributed X-ray source that generates an electron beams stream by hot cathodes, scans at low energy, limits current to produce a distribution of array then performs high voltage acceleration and hits targets to generate X-ray. It further manufactures a cathode control multi-cathode distributed X-ray apparatus, exhibiting a distributed X-ray source where a plurality of cathode arrays are controlled in a certain order to generate an electron beam stream which, after being focused and limited, accelerates at high voltage and hits targets to generate X-ray. It may be a straight line or an arc structure. Using said distributed X-ray sources, and through flexible structural arrangement, this invention acquires many types of goods inspection apparatus capable of satisfying different application requirements.

CONTENTS OF THE INVENTION

This invention is put forward to solve the above problems, aiming to provide a goods inspection apparatus using distributed X-ray source, being able to acquire 3-D perspective image information of an object under inspection.

This invention provides a goods inspection apparatus, comprising:

A frame;

A goods passage in the frame for the object under inspection to pass;

A goods conveyor in the frame and below the goods passage;

A distributed X-ray source above the goods passage, being able to produce X-ray at different positions successively within each working cycle;

A detector array composed of a plurality of detectors below the goods passage and arranged symmetrically with the distributed X-ray source around the goods passage, for receiving the X-ray from the distributed X-ray source and outputting signals indicating the strength of the X-ray;

An electronics system, for receiving signals from the detectors, converting the signals into digital ones, and forming a data packet with the position numbers of corresponding detectors, outputting a sequence of data packets formed by the position numbers and signals from the plurality of detectors of the detector array;

An image processing system, for receiving the output from the electronics system, using a reconstruction algorithm to process the position numbers of detectors and the corresponding signals indicating the strength of X-ray, constructing to form an image of the object under inspection;

A ray source power supply, for providing power to the distributed X-ray source; and A control system, for exercising logical control over the respective parts to enable the respective sub-systems to work in coordination.

This invention provides a goods inspection apparatus, comprising:

A frame;

A goods passage in the frame for the object under inspection to pass;

A goods conveyor in the frame and below the goods passage;

A first distributed X-ray source above the goods passage, being able to produce X-ray at different positions successively within each working cycle;

A second distributed X-ray source at the left side of the goods passage, being able to produce X-ray at different positions successively within each working cycle;

A first detector array composed of a plurality of detectors below the goods passage and arranged symmetrically with the first distributed X-ray source around the goods passage, for receiving the X-ray from the first distributed X-ray source and outputting signals indicating the strength of the X-ray;

A second detector array composed of a plurality of detectors on the right of the goods passage and arranged symmetrically with the second distributed X-ray source around the goods passage, for receiving the X-ray from the second distributed X-ray source and outputting signals indicating the strength of the X-ray;

An electronics system, for receiving signals from the detectors, converting the signals into digital ones, and forming a data packet with the position numbers of corresponding detectors, outputting a sequence of data packets formed by the position numbers and signals from the plurality of detectors of the first and second detector arrays;

An image processing system, for receiving the output from the electronics system, using a reconstruction algorithm to process the position numbers of detectors and the corresponding signals indicating the strength of X-ray, constructing to form an image of the object under inspection;

A ray source power supply, for providing power to the distributed X-ray source; and A control system, for exercising logical control over the respective parts to enable the respective sub-systems to work in coordination.

This invention provides a goods inspection apparatus, comprising:

A frame;

A goods passage in the frame for the object under inspection to pass;

A goods conveyor in the frame and below the goods passage;

A first distributed X-ray source in a first plane perpendicular to the direction of travel of the object under inspection and arranged above the goods passage;

A first detector array composed of a plurality of detectors, being arranged in the first plane below the goods passage opposite the first distributed X-ray source, for receiving the X-ray from the first distributed X-ray source and outputting signals indicating the strength of the X-ray;

A second distributed X-ray source in a second plane perpendicular to the direction of travel of the object under inspection and arranged above the goods passage;

A second detector array composed of a plurality of detectors, being arranged in the second plane below the goods passage opposite the second distributed X-ray source, for receiving the X-ray from the second distributed X-ray source and outputting signals indicating the strength of the X-ray;

An electronics system, for receiving signals from the detectors, converting the signals into digital ones, and forming a data packet with the position numbers of corresponding detectors, outputting a sequence of data packets formed by the position numbers and signals from the plurality of detectors of the first and second detector arrays;

An image processing system, for receiving the output from the electronics system, using a reconstruction algorithm to process the position numbers of detectors and the corresponding signals indicating the strength of X-ray, constructing to form an image of the object under inspection;

A ray source power supply, for providing power to the distributed X-ray source; and A control system, for exercising logical control over the respective parts to enable the respective sub-systems to work in coordination.

This invention provides a goods inspection apparatus, comprising:

A frame;

A circular goods passage in the frame for the object under inspection to pass;

A goods conveyor in the frame and below the goods passage;

An arc-shaped distributed X-ray source in a first plane perpendicular to the direction of travel of the object under inspection and arranged above the goods passage;

An arc-shaped detector array composed of a plurality of detectors, being arranged below the goods passage, for receiving the X-ray from the arc-shaped distributed X-ray source and outputting signals indicating the strength of the X-ray;

An electronics system, for receiving signals from the detectors, converting the signals into digital ones, and forming a data packet with the position numbers of corresponding detectors, outputting a sequence of data packets formed by the position numbers and signals from the plurality of detectors of the detector array;

An image processing system, for receiving the output from the electronics system, using a reconstruction algorithm to process the position numbers of detectors and the corresponding signals indicating the strength of X-ray, constructing to form an image of the object under inspection;

A ray source power supply, for providing power to the distributed X-ray source; and A control system, for exercising logical control over the respective parts to enable the respective sub-systems to work in coordination.

This invention provides a goods inspection apparatus, comprising:

A frame;

A circular goods passage in the frame for the object under inspection to pass;

A goods conveyor in the frame and below the goods passage;

A plurality of arc-shaped distributed X-ray sources arranged as a complete circle in a first plane perpendicular to the direction of travel of the object under inspection;

A plurality of detector arrays arranged as a complete circle in a second plane adjacent to the first plane perpendicular to the direction of travel of the object under inspection, each array being composed of a plurality of detectors, and the arrangement of the detector array has a predetermined angle of inclination, so that the X-ray from the arc-shaped distributed X-ray source enters the detector array vertically;

An electronics system, for receiving signals from the detectors, converting the signals into digital ones, and forming a data packet with the position numbers of corresponding detectors, outputting a sequence of data packets formed by the position numbers and signals from the plurality of detectors of the detector array;

An image processing system, for receiving the output from the electronics system, using a reconstruction algorithm to process the position numbers of detectors and the corresponding signals indicating the strength of X-ray, constructing to form an image of the object under inspection;

A ray source power supply, for providing power to the distributed X-ray source; and A control system, for exercising logical control over the respective parts to enable the respective sub-systems to work in coordination.

The goods inspection apparatus of the present invention further comprises:

A shielding apparatus mounted in the frame for shielding other useless scattered X-ray;

A cooling apparatus mounted in the frame for cooling off the respective parts of the goods inspection apparatus, and An X-ray collimator secured to the ray exit of the distributed X-ray source, for useful X-ray to pass and enter the goods passage.

In the goods inspection apparatus of the present invention, the structure of the detector array is as follows:

Each detector array is composed of a column of detectors or of many columns of detectors in parallel arrangement along the direction of travel of the object under inspection.

In the goods inspection apparatus of the present invention, the distributed X-ray apparatus comprises:

A vacuum box with the perimeter sealed and a high vacuum inside;

A plurality of cathodes independent of each other and arranged as a linear array at one end inside the vacuum box, each cathode having a cathode filament, a cathode surface connected to the cathode filament and a filament lead drawn out from both ends of the cathode filament;

A plurality of focal current limiters arranged in a linear array corresponding one by one to the cathodes at a position near the cathodes in the middle part inside the vacuum box, the focal current limiters being connected to one another;

An anode made of strip-shaped metal and mounted at another end inside the vacuum box, being parallel to the focal current limiters in the length direction and forming an included angle of several to a dozen of degrees with the focal current limiters in the width direction;

A power supply and control system, having a plurality of cathode power supplies, a focal current limiter power supply connected to the interconnected focal current limiters, an anode high voltage power supply, and a control apparatus exercising comprehensive control over the respective power supplies;

A pluggable high voltage connector, for connecting the anode to the cable of the anode high voltage power supply, and installed at the side face of one end of the vacuum box near the anode; and A plurality of pluggable cathode power supply connectors, for connecting the cathode to the cathode power supply, and installed at the side face of one end of the vacuum box near the cathode.

In the goods inspection apparatus of the present invention, the distributed X-ray apparatus comprises:

An electron gun, for generating an electron beam stream;

A deflector surrounding the electron beam stream for generating a scanning magnetic field to deflect the electron beam stream;

A current limiter with a plurality of regularly arranged apertures, and when the electron beam stream scans the plurality of apertures of the current limiter under the control of the deflector, the current limiter outputs a pulsed electron beam;

An accelerator arranged downstream the current limiter to accelerate the pulsed electron beam;

An anode target, where the accelerated electron beam bombards the anode target to generate X-ray.

Therefore, this invention provides a goods inspection apparatus using distributed X-ray source, which is able to acquire X-ray images of an object under inspection from multiple angles of view without having to move the X-ray source, and can obtain a 3D image of the object under inspection through a software algorithm of the image processing system, with such advantages as simple structure, low cost and quick examination. Besides, by multiple structural designs, different objectives of application can be achieved such as low cost, or high speed, or high image quality, or combination thereof.

EXPLANATIONS OF REFERENCE SIGNS

1 distributed X-ray source
2 ray collimator
3 ray source power supply
4 detector
5 shielding apparatus
6 goods conveyor
7 power supply
8 electronics system
9 cooling apparatus
10 image processing system
11 control system
12 frame
13 goods passage
14, 14a, 14b, 14c X-ray
15 object under inspection

MODE FOR CARRYING OUT THE INVENTION

Following are explanations of the mode of carrying out the invention with reference to the figures.

Figure 1:
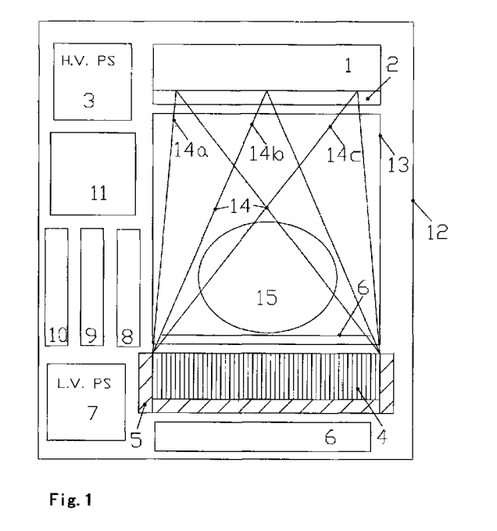
FIG. 1 is a schematic diagram of the structure of the goods inspection apparatus using distributed X-ray source.

The goods inspection apparatus using distributed X-ray source in this invention has one or more distributed X-ray sources 1, one or more ray collimators 2, one or more ray source power supplies 3, one or more detector arrays 4, a shielding apparatus 5, a goods conveyor 6, a power supply 7, an electronics system 8, a cooling apparatus 9, an image processing system 10, a control system 11, a frame 12, a goods passage 13, and so on. The goods passage 13 is in the frame 12. The goods conveyor 6 is below the goods passage 13. The distributed X-ray source 1 and detector array 4 are arranged symmetrically surrounding the goods passage 13. The ray collimator 2 is secured to the ray exit of the distributed X-ray source 1. Other parts and sub-systems are scattered inside the frame 12 or on the surface of the frame 12.

Under the action of the ray source power supply 3, the distributed X-ray source 1 generates an X-ray 14 whose target spot position changes in a predetermined order, for example, X-rays 14a, 14b, 14c have different target spot positions and a predetermined order of emission. The ray collimator 2 causes useful X-ray to pass and enter the goods passage 13 and shields the disorderly useless X-ray, such that the useful X-ray generated by each target spot, after transmitting the goods passage 13, can cover all detectors of the detector array 4. The goods conveyor 6 carries the object under inspection 15 through the X-ray radiation region. Passing through the object under inspection 15, the X-ray attenuates in strength relative to the density and thickness of the object under inspection 15. The detector of the detector array 4 receives the X-ray from the distributed X-ray source 1, outputs a signal indicating the X-ray strength to the electronics system 8. When the X-ray passes through the object under inspection 15, due to such influencing factors as the volume, shape and density of the object under inspection 15, the X-ray in different directions will attenuate differently in strength. The various detectors of the detector array 4 receive different X-ray strength information, which reflects the thickness, density and other structural information of the object under inspection 15 passing through the connecting line from the X-ray target spot to the detectors of the detector array 4. The electronics system 8 converts the signals from detectors into digital signals, and forms a data packet with the position numbers of corresponding detectors. Besides, the electronics system 8 sends a sequence of data packets formed by the position numbers of detectors and signals from the plurality of detectors of the detector array 4 to the image processing system 10. The image processing system 10 uses a reconstruction algorithm to process the position numbers of detectors and the corresponding signals indicating the strength of X-ray, thus being capable of constructing the processed data to form an image of the object under inspection 15. The distributed X-ray source 1 quickly changes the target spot position of the X-ray. The X-ray generated at different positions passes through the object under inspection 15 and arrives at the detector array 4. This is equivalent to X-raying the object under inspection 15 from angles of views at different positions. The image processing system 10 analyzes and reconstructs the image information from different angles of view, thereby acquiring a 2D section image of the object under inspection 15. The goods conveyor 6 carries the object under inspection 15 through the X-ray radiation region at a certain speed, thus obtaining a series of 2D section images of the object under inspection 15 along the direction of travel. The image processing system 10 analyzes and reconstructs these section images, thus obtaining a 3D image of the object under inspection 15. The image processing system 10 then displays the 3D image of the object under inspection 15 in real time, so the staff can perform defect analysis, structure analysis and object type analysis of the object under inspection 15 based on said 3D image, thereby achieving the respective particular purposes of inspection. The shield apparatus 5 is to eliminate the influence of disorderly X-ray on the detector array, and improve the image resolution. Besides, the shielding apparatuses mounted at other positions inside the frame are to shield the scattered X-ray from other directions, thus ensuring the safety of the staff and other personnel near the device. The cooling apparatus 9 cools off the distributed X-ray source 1, detector array 4, electronics system 8, power supply 7 and so on, such that the respective components maintain a stable operating state. The control system 11 exercises a logical control over the various parts so that the sub-systems operate in coordination, and at the same time, provides the control program and operation interface for the staff to operate the whole device.

The distributed X-ray source 1 is to generate an X-ray that changes target spot position in a predetermined order. In the above goods inspection apparatus, there may be a distributed X-ray source 1, or a plurality of distributed X-ray sources 1 distributed about the goods passage 13, with a or a plurality of corresponding detector arrays. A plurality of distributed X-ray sources 1 and a plurality of detector arrays are arranged in a circle on the same plane, thus being able to acquire image quality of higher resolution from more angles of view. A plurality of distributed X-ray sources 1 and a plurality of detector arrays are arranged at different positions in the direction of travel of the object under inspection 15, thus being able to achieve faster inspection speed.

The distributed X-ray sources 1 and detector arrays may have a straight line structure or an arc structure. In the case of the distributed X-ray sources 1 and detector arrays being a straight line structure, a goods passage with a squire cross section is formed; and in the case of an arc structure, a circular goods passage is formed.

The detector array may be an arrangement of single column of detectors, and for each beam cycle of the distributed X-ray sources 1, the system acquires a section image. The detector array may also be an arrangement of multiple columns of detectors, and for each beam cycle of the distributed X-ray sources 1, the system acquires a plurality of section images, forming a system having an arrangement of multiple columns of detectors, thereby greatly increasing the goods inspection speed.

The detector arrays and the distributed X-ray sources 1 may be arranged on the same plane, or on two adjacent planes. In the direction of travel of the object under inspection 15, there may be one or more distributed X-ray sources 1 on a plane perpendicular to the direction of travel of the object under inspection 15 until a whole circle is fully arranged. One or more detector arrays 4 are arranged corresponding to the distributed X-ray sources 1 on a plane adjacent to the above one until a whole circle is fully arranged.

FIG. 1 shows the structure of the goods inspection apparatus using distributed X-ray source. Disposed above the goods passage 13 is a distributed X-ray source 1, which is able to produce X-ray successively at different positions within each working cycle, e.g., 14a→14b→14c. The detector array 4 is disposed below the goods passage 13 opposite to the distributed X-ray source 1. Other parts and sub-systems are scattered in the frame. This apparatus uses a distributed X-ray source 1, thus being able to acquire a 3D image of the object under inspection 15. Besides, this apparatus has such advantages as simple structure, low cost and so on.

Figure 2:
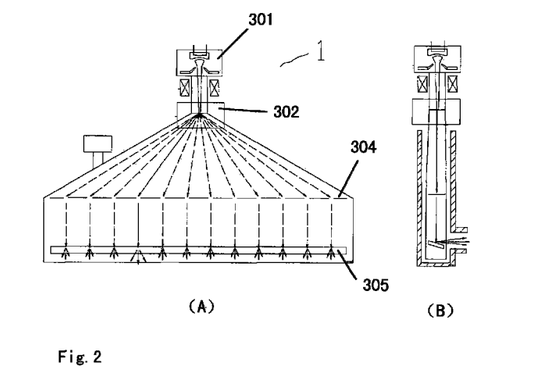
FIG. 2 is a schematic diagram of the structure of a distributed X-ray source used in the present invention.

FIG. 2 shows the structure of the distributed X-ray source 1, (A) is a schematic diagram, (B) is a side view. This distributed X-ray source 1 has a flat structure, so can be placed horizontally and applied to the goods inspection apparatus using distributed X-ray source. The distributed X-ray source 1 generates a low energy electron beam by a hot cathode electron gun. The low energy electron beam is focused and scanned, and projected to a current limiting plate. Through the beam stream aperture on the current limiting plate, the electron beam enters a parallel electric field to gain acceleration and high energy, and bombard the anode target in the end, generating X-ray successively at different positions of the anode target. To be specific, as shown by FIG. 2, the distributed X-ray source 1 comprises: an electron gun 301, for generating an electron beam stream; a deflector 302 surrounding the electron beam stream for generating a scanning magnetic field to deflect the electron beam stream; a current limiter 304 with a plurality of regularly arranged apertures, and when the electron beam stream scans the plurality of apertures of the current limiter 304 under the control of the deflector 302, the current limiter 304 outputs a pulsed electron beam; an accelerator arranged downstream the current limiter 304 to accelerate the pulsed electron beam; an anode target 305, where the accelerated electron beam bombards the anode target 305 to generate X-ray.

During the working process of the distributed X-ray source 1, the electron beam stream from the electron gun 301 is projected through the deflector 302 to the beam spot on the current limiter 304 to move left and right with the size of the magnetic field B generated by the deflector 302, but the electron beam spot can only cover one aperture therein, so at a certain definite time the electron beam stream can always pass through only one aperture on the current limiter 304, i.e., all electron beam streams entering the high voltage electric field between the current limiter and the anode through the aperture of the current limiter 304 for accelerated movement are concentrated on one aperture position, bombard the anode in the end and form an X-ray target spot. Besides, with the change of time, the electron beam spot moves on the current limiter, and the aperture covered by the electron beam spot will also move to the next one, then the electron beam stream will pass through the next aperture and form a next X-ray target spot at the corresponding anode.

Figure 3:
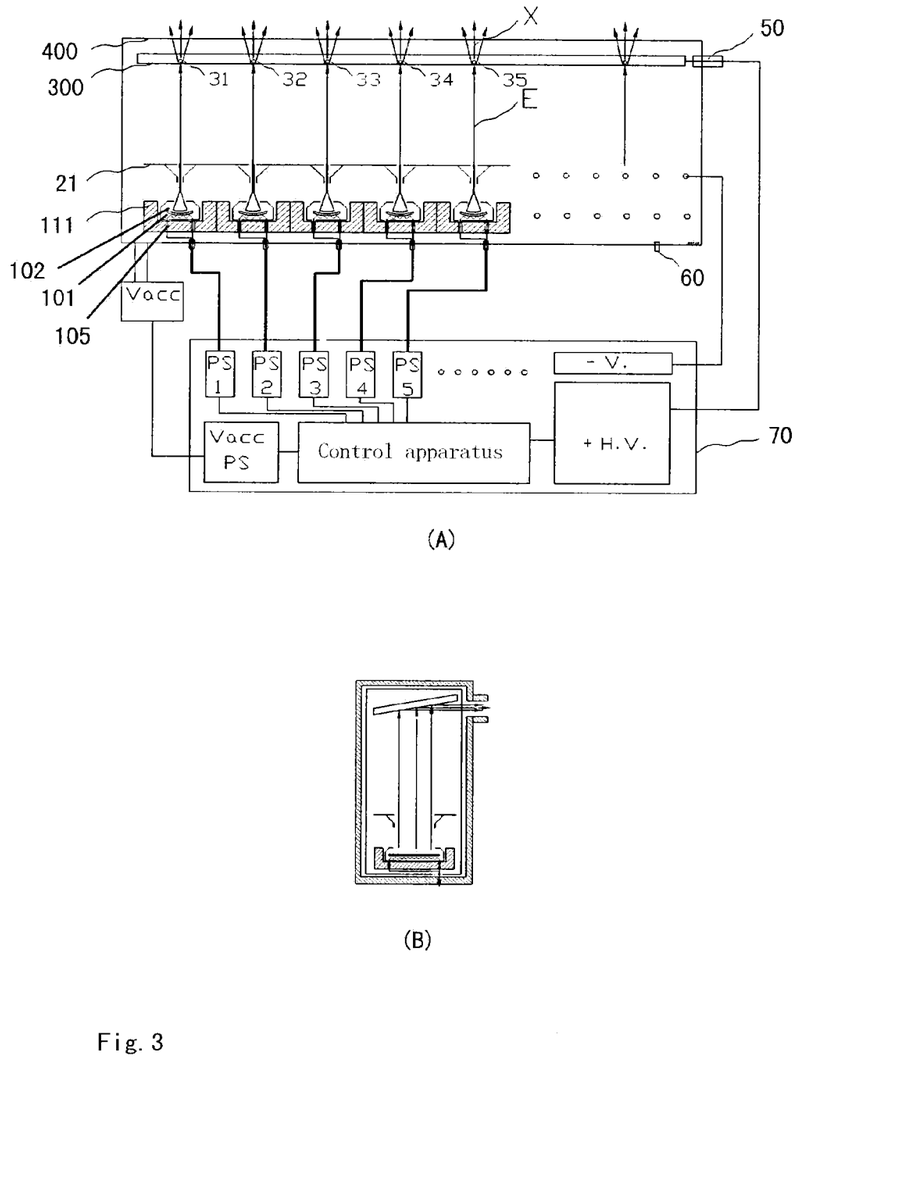
FIG. 3 is a schematic diagram of the structure of another distributed X-ray source used in the present invention.

FIG. 3 shows the structure of another distributed X-ray source 1, (A) is a schematic diagram, (B) is a side view. This distributed X-ray source 1 has a flat structure or a ring structure, so can be placed horizontally and applied to the goods inspection apparatus using distributed X-ray source. The distributed X-ray source 1 generates electrons by a plurality of hot cathodes arranged in an array. Limited by focal current limiters, the electrons usually cannot be emitted. Only when the cathode is under the action of the negative high voltage pulse of the cathode power supply will the electrons be emitted and focused and limited, thereafter enter a parallel high voltage electric field to acquire acceleration and high energy, and bombard the anode target. By controlling the work sequence of the negative high voltage pulse of the cathode we will be able to generate distributed X-ray in a predetermined order at different positions of the anode target. Besides, the distributed X-ray source can be flexibly designed into a straight line or an arc.

To be more specific, the distributed X-ray apparatus 1 comprises: a vacuum box 400 with the perimeter sealed and a high vacuum inside; a plurality of cathodes 111 independent of each other and arranged as a linear array at one end inside the vacuum box 400, each cathode 111 having a cathode filament 101, a cathode surface 102 connected to the cathode filament 101 and a filament lead 105 drawn out from both ends of the cathode filament 1001; a plurality of focal current limiters 21 arranged in a linear array corresponding one by one to the cathodes 111 at a position near the cathodes 111 in the middle part inside the vacuum box 400, the focal current limiters 21 being connected to one another; an anode 300 made of rectangular metal and mounted at another end inside the vacuum box 400, being parallel to the focal current limiters 21 in the length direction and forming an included angle of several to about a dozen of degrees with the focal current limiters 21 in the width direction; a power supply and control system 70, having a cathode power supply, a focal current limiter power supply connected to the interconnected focal current limiters, an anode high voltage power supply, and a control apparatus exercising comprehensive control over the respective power supplies; a pluggable high voltage connector 50, for connecting the anode 300 to the cable of the anode high voltage power supply, and installed at the side face of one end of the vacuum box 400 near the anode 300; a plurality of pluggable cathode power supply connectors 60, for connecting the cathodes 111 to the cathode power supply, and installed at the side face of one end of the vacuum box 400 near the cathodes 111. In this distributed X-ray apparatus 1, by the control of the power supply and control system 70, X-ray that periodically changes focal positions in a predetermined order can be generated.

To be more specific, for example, in the above distributed X-ray apparatus 1, by the control of the power supply and the control system 70, the cathode power supplies (PS1, PS2, PS3, . . . ), focal current limiter power supply −V., vacuum power supply Vacc PS, anode high voltage power supply +H.V. and the like are made to work according to a preset program. The cathode power supply supplies power to cathode filament, which heats cathode surface up to a very high temperature to generate a great amount of thermal emitting electrons. The focal current limiter power supply applies a negative voltage of 200V to the interconnected focal current limiters, forming a reversed electric field at the beam stream aperture of each of cathodes, thereby limiting the hot electrons of cathode surface from flying out of cathode housing. The anode high voltage power supply provides a positive voltage of 160 kV to the anode, forming a positive high voltage electric field between the array of focal current limiters and the anode. Time 1: the power supply and control system controls the cathode power supply to generate a negative high voltage pulse of 2 kV and supply to a cathode, the overall voltage of the cathode has a pulse-like drop, such that the electric field between the cathode and focal current limiters becomes a positive electric field instantly, the thermal electrons in the cathode housing of the cathode emits out from the beam stream aperture, flying to the focus electrode of focal current limiters. The thermal electrons, being focused during the movement, becomes a small size of electron beam stream, and most of which enters the central aperture of the focus electrode, and arrives at the current limiting aperture after a short period of drift motion. Marginal and less forward electrons are blocked by the current limiting structure around current limiting aperture. Only the electron beams that are consistently forward and concentrated at a small range pass through the current limiting aperture to enter the positive high voltage electric field and are accelerated to acquire energy, and in the end, bombard the anode to generate X-ray. The focal position of X-ray is a focus 31. Likewise, time 2 is focal position 32, time 3 is focal position 33; . . . until the last cathode emits a beam stream and produces the last focal position, thus completing a work cycle. At the next cycle, repeat the focal positions 31, 32, 33, 34, . . . to generate X-ray successively.

The above are structures of two types of distributed X-ray apparatus, but they are not limited thereto. All X-ray apparatuses capable of generating X-ray at different positions successively within each work cycle are applicable to the invention of this application.

Figure 4:
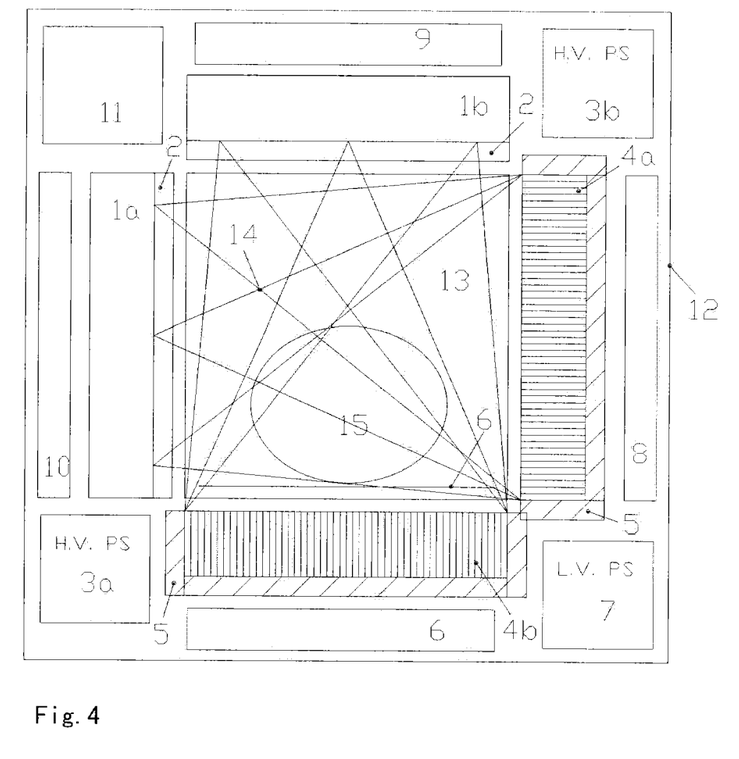
FIG. 4 is a schematic diagram of the structure of another goods inspection apparatus using distributed X-ray source.

Besides, FIG. 4 shows the structure of a goods inspection apparatus using a plurality of distributed X-ray sources. In one and the same plane perpendicular to the direction of travel of the object under inspection 15, a distributed X-ray source 1b is disposed above the goods passage 13, while the corresponding detector array 4b is disposed below the goods passage 13 opposite to the distributed X-ray source 1b. The other distributed X-ray source 1a is disposed on the left of the goods passage 13, while the corresponding detector array 4a is disposed on the right of the goods passage 13 opposite to the distributed X-ray source 1a. Other parts and sub-systems are scattered in the frame. In this apparatus, a plurality of distributed X-ray sources are disposed, thus being able to acquire an high definition 3D image of the object under inspection.

Figure 5:
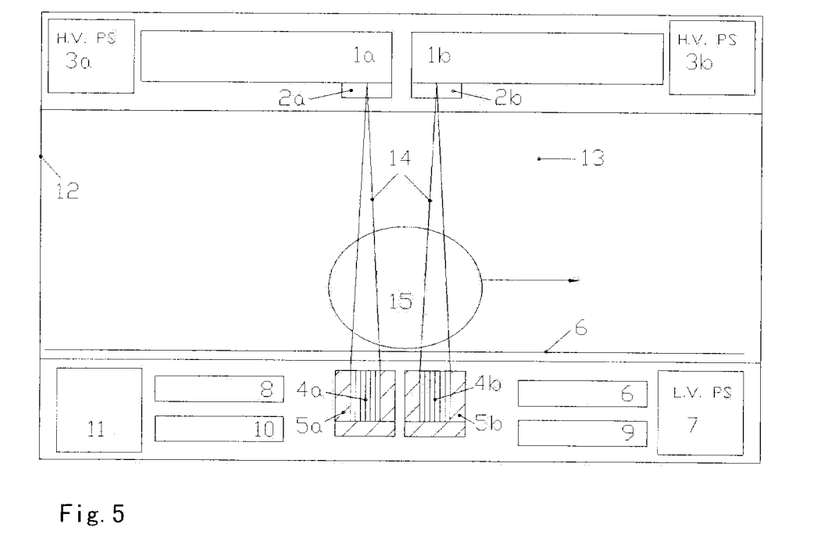
FIG. 5 is a schematic diagram of the side structure of another goods inspection apparatus using distributed X-ray source.

FIG. 5 is a schematic diagram of the side structure of another goods inspection apparatus using distributed X-ray source. In a first plane perpendicular to the direction of travel of the object under inspection 15, a distributed X-ray source 1a is disposed above the goods passage 13, while the corresponding detector array 4a is disposed below the goods passage 13 opposite to the distributed X-ray source 1a. Besides, in a second plane perpendicular to the direction of travel of the object under inspection 15, another distributed X-ray source 1b is disposed above the goods passage 13, while the corresponding detector array 4b is disposed below the goods passage 13 opposite to the distributed X-ray source 1b. Each detector array is an arrangement of multiple columns of detectors, for example, six columns of detectors are arranged into an array in the direction of travel of the object under inspection 15. The image processing system 10 makes a comprehensive reconstruction of the image information obtained by a plurality of distributed X-ray sources and corresponding detector arrays. Other parts and sub-systems are scattered in the frame. In this apparatus, a plurality of distributed X-ray sources are disposed, thus being able to multiply the goods inspection speed.

Figure 6:
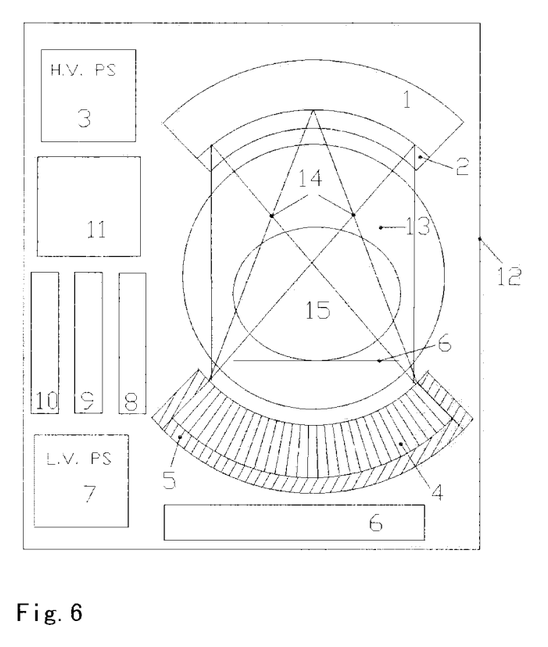
FIG. 6 is a schematic diagram of the structure of a goods inspection apparatus using arc-shaped distributed X-ray source.

FIG. 6 shows the structure of a goods inspection apparatus using arc-shaped distributed X-ray source. In a plane perpendicular to the direction of travel of the object under inspection 15, an arc-shaped distributed X-ray source 1 is disposed above the goods passage 13, while the corresponding arc-shaped detector array 4 is disposed below the goods passage 13 opposite to the arc-shaped distributed X-ray source 1. In the inspection apparatus, the goods passage 13 is circular. In the goods inspection apparatus using the arc-shaped distributed X-ray source 1, for the X-ray generated at different positions, every detector in the detector array is in a pretty ideal ray receiving angle. As compared with the straight line solution, this is conducive to improving the image quality.

Figure 7:
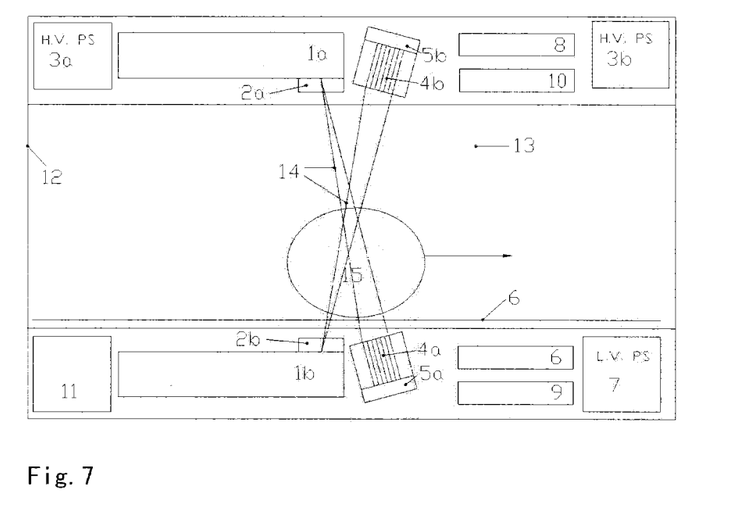
FIG. 7 is a schematic diagram of the side structure of a goods inspection apparatus using a plurality of arc-shaped distributed X-ray sources.

FIG. 7 is a schematic diagram of the side structure of a goods inspection apparatus using a plurality of arc-shaped distributed X-ray sources. In a first plane perpendicular to the direction of travel of the object under inspection 15, a plurality of arc-shaped distributed X-ray sources (1a, 1b, ...) are arranged to a complete circle. In a second plane adjacent to the first plane perpendicular to the direction of travel of the object under inspection 15, a plurality of detector arrays (4a, 4b, ...) are arranged to a complete circle. The ray collimator 2 at the ray exit of the distributed X-ray source 1 collimates the outgoing direction of the X-ray to the plane where the detector array is located, and the arrangement of the detector array has a predetermined angle of inclination to facilitate the vertical incidence of X-ray. Besides, every detector array is an arrangement of multiple rows detectors, for example, six rows of detects are arranged in an array in the direction of travel of the object under inspection. Other parts and sub-systems are scattered in the frame. In this apparatus, a plurality of arc-shaped distributed X-ray sources are arranged in a complete circle, thus being able to improve the image quality of the object under inspection to the maximum degree.

It should be noted that synthesizing the above solutions of arrangement can achieve a comprehensive effect of low cost, high speed and high quality of images.

Besides, this invention does not exhaust the passage shapes of the above solutions of arrangement, such as square, rectangle, circle, oval and so on, and the number and positions of the distributed X-ray source, the number and positions of the detector arrays and the positions relative to the distributed X-ray source. No simple alternations, modifications or combinations made on the basis of this invention's solutions of arrangement go beyond the spirit and scope of protection of this invention.

(Effect)

The present invention provides a goods inspection apparatus using distributed X-ray source that is capable of acquiring an X-ray image of the object under inspection from a plurality of angles of view without having to move the light source, and is able to obtain a 3D image of the object under inspection through a software algorithm of the image processing system, having such merits as simple structure, low cost, quick examination and so on. Besides, by multiple structural designs, this invention can satisfy different purposes of application such as low cost, or high speed, or high image quality, or a combination of multiple effects.

The invention claimed is:

1. A goods inspection apparatus, characterized by comprising:
   a frame;
   a goods passage in the frame for an object under inspection to pass;
   a goods conveyor in the frame and below the goods passage;
   a distributed X-ray source above the goods passage, being able to produce X-ray at different positions successively within each working cycle;
   a detector array composed of a plurality of detectors below the goods passage and arranged symmetrically with the distributed X-ray source around the goods passage, for receiving the X-ray from the distributed X-ray source and outputting signals indicating the strength of the X-ray;
   a ray collimator, for enabling X-ray generated by the distributed X-ray source to cover all detectors of the detector array after transmitting the goods passage;
   an electronics system, for receiving signals from the detectors, converting the signals into digital ones, and forming a data packet with the position numbers of corresponding detectors, outputting a sequence of data packets formed by the position numbers and signals from the plurality of detectors of the detector array;
   an image processing system, for receiving the output from the electronics system, using a reconstruction algorithm to process the position numbers of detectors and the corresponding signals indicating the strength of X-ray, constructing to form an image of the object under inspection;
   a ray source power supply, for providing power to the distributed X-ray source; and a control system, for exercising logical control over the respective parts to enable respective sub-systems to work in coordination.

2. A goods inspection apparatus, characterized by comprising:

a frame;

a goods passage in the frame for an object under inspection to pass;

a goods conveyor in the frame and below the goods passage;

a first distributed X-ray source above the goods passage, being able to produce X-ray at different positions successively within each working cycle;

a second distributed X-ray source at the left side of the goods passage, being able to produce X-ray at different positions successively within each working cycle;

a first detector array composed of a plurality of detectors below the goods passage and arranged symmetrically with the first distributed X-ray source around the goods passage, for receiving the X-ray from the first distributed X-ray source and outputting signals indicating the strength of the X-ray;

a first ray collimator, for enabling X-ray generated by the first distributed X-ray source to cover all detectors of the first detector array after transmitting the goods passage;

a second ray collimator, for enabling X-ray generated by the second distributed X-ray source to cover all detectors of the second detector array after transmitting the goods passage;

a second detector array composed of a plurality of detectors on the right of the goods passage and arranged symmetrically with the second distributed X-ray source around the goods passage, for receiving the X-ray from the second distributed X-ray source and outputting signals indicating the strength of the X-ray;

an electronics system, for receiving signals from the detectors, converting the signals into digital ones, and forming a data packet with the position numbers of corresponding detectors, outputting a sequence of data packets formed by the position numbers and signals from the plurality of detectors of the first and second detector arrays;

an image processing system, for receiving the output from the electronics system, using a reconstruction algorithm to process the position numbers of detectors and the corresponding signals indicating the strength of X-ray, constructing to form an image of the object under inspection;

a ray source power supply, for providing power to the distributed X-ray source; and a control system, for exercising logical control over the respective parts to enable respective sub-systems to work in coordination.

3. A goods inspection apparatus, characterized by comprising:

a frame;

a goods passage in the frame for an object under inspection to pass;

a goods conveyor in the frame and below the goods passage;

a first distributed X-ray source in a first plane perpendicular to the direction of travel of the object under inspection and arranged above the goods passage;

a first detector array composed of a plurality of detectors, being arranged in the first plane below the goods passage opposite the first distributed X-ray source, for receiving the X-ray from the first distributed X-ray source and outputting signals indicating the strength of the X-ray;

a first ray collimator, for enabling X-ray generated by the first distributed X-ray source to cover all detectors of the first detector array after transmitting the goods passage;

a second distributed X-ray source in a second plane perpendicular to the direction of travel of the object under inspection and arranged above the goods passage;

a second detector array composed of a plurality of detectors, being arranged in the second plane below the goods passage opposite the second distributed X-ray source, for receiving the X-ray from the second distributed X-ray source and outputting signals indicating the strength of the X-ray;

a second ray collimator, for enabling X-ray generated by the second distributed X-ray source to cover all detectors of the second detector array after transmitting the goods passage;

an electronics system, for receiving signals from the detectors, converting the signals into digital ones, and forming a data packet with the position numbers of corresponding detectors, outputting a sequence of data packets formed by the position numbers and signals from the plurality of detectors of the first and second detector arrays;

an image processing system, for receiving the output from the electronics system, using a reconstruction algorithm to process the position numbers of detectors and the corresponding signals indicating the strength of X-ray, constructing to form an image of the object under inspection;

a ray source power supply, for providing power to the distributed X-ray source; and a control system, for exercising logical control over the respective parts to enable respective sub-systems to work in coordination.

4. A goods inspection apparatus, characterized by comprising:

a frame;

a circular goods passage in the frame for an object under inspection to pass;

a goods conveyor in the frame and below the goods passage;

an arc-shaped distributed X-ray source in a first plane perpendicular to the direction of travel of the object under inspection and arranged above the goods passage;

an arc-shaped detector array composed of a plurality of detectors, being arranged below the goods passage, for receiving the X-ray from the arc-shaped distributed X-ray source and outputting signals indicating the strength of the X-ray;

a ray collimator, for enabling X-ray generated by the arc-shaped distributed X-ray source to cover all detectors of the arc-shaped detector array after transmitting the goods passage;

an electronics system, for receiving signals from the detectors, converting the signals into digital ones, and forming a data packet with the position numbers of corresponding detectors, outputting a sequence of data packets formed by the position numbers and signals from the plurality of detectors of the detector array;

an image processing system, for receiving the output from the electronics system, using a reconstruction algorithm to process the position numbers of detectors and the corresponding signals indicating the strength of X-ray, constructing to form an image of the object under inspection;

a ray source power supply, for providing power to the distributed X-ray source; and a control system, for exercising logical control over the respective parts to enable respective sub-systems to work in coordination.

5. A goods inspection apparatus, comprising:

a frame;

a circular goods passage in the frame for an object under inspection to pass;

a goods conveyor in the frame and below the goods passage;

a plurality of arc-shaped distributed X-ray sources arranged as a complete circle in a first plane perpendicular to the direction of travel of the object under inspection;

a plurality of detector arrays arranged as a complete circle in a second plane adjacent to the first plane perpendicular to the direction of travel of the object under inspection, each array being composed of a plurality of detectors, and the arrangement of the detector array has a predetermined angle of inclination, so that the X-ray from the arc-shaped distributed X-ray source enters the detector array vertically;

a plurality of ray collimators, for enabling X-ray generated by the plurality of arc-shaped distributed X-ray sources to cover all detectors of the plurality of detector arrays after transmitting the goods passage;

an electronics system, for receiving signals from the detectors, converting the signals into digital ones, and forming a data packet with the position numbers of corresponding detectors, outputting a sequence of data packets formed by the position numbers and signals from the plurality of detectors of the detector array;

an image processing system, for receiving the output from the electronics system, using a reconstruction algorithm to process the position numbers of detectors and the corresponding signals indicating the strength of X-ray, constructing to form an image of the object under inspection;

a ray source power supply, for providing power to the distributed X-ray source; and a control system, for exercising logical control over the respective parts to enable respective sub-systems to work in coordination.

6. The goods inspection apparatus according to any one of claims 1-5, characterised by further comprising:

a shielding apparatus mounted in the frame for shielding other useless scattered X-ray;

a cooling apparatus mounted in the frame for cooling off the respective parts of the goods inspection apparatus, and an X-ray collimator secured to the ray exit of the distributed X-ray source, for useful X-ray to pass and enter the goods passage, each detector array is composed of a column of detectors or of many columns of detectors in parallel arrangement along the direction of travel of the object under inspection.

7. The goods inspection apparatus according to any one of claims 1-5, characterised in that, the distributed X-ray apparatus comprises:

a vacuum box with the perimeter sealed and a high vacuum inside;

a plurality of cathodes independent of each other and arranged as a linear array at one end inside the vacuum box, each cathode having a cathode filament, a cathode surface connected to the cathode filament and a filament lead drawn out from both ends of the cathode filament;

a plurality of focal current limiters arranged in a linear array corresponding one by one to the cathodes at a position near the cathodes in the middle part inside the vacuum box, the focal current limiters being connected to one another;

an anode made of metal and mounted at another end inside the vacuum box, being parallel to the focal current limiters in the length direction and forming an included angle of several to a dozen of degrees with the focal current limiters in the width direction;

a power supply and control system, having a plurality of cathode power supplies, a focal current limiter power supply connected to the interconnected focal current limiters, an anode high voltage power supply, and a control apparatus exercising comprehensive control over the respective power supplies;

a pluggable high voltage connector, for connecting the anode to the cable of the anode high voltage power supply, and installed at the side face of one end of the vacuum box near the anode; and a plurality of pluggable cathode power supply connectors, for connecting the cathode to the cathode power supply, and installed at the side face of one end of the vacuum box near the cathode.

8. The goods inspection apparatus according to any one of claims 1-5, characterised ion that, the distributed X-ray apparatus comprises:

an electron gun, for generating an electron beam stream;

a deflector surrounding the electron beam stream for generating a scanning magnetic field to deflect the electron beam stream;

a current limiter with a plurality of regularly arranged apertures, and when the electron beam stream scans the plurality of apertures of the current limiter under the control of the deflector, the current limiter outputs a pulsed electron beam;

an accelerator arranged downstream the current limiter to accelerate the pulsed electron beam;

an anode target, where the accelerated electron beam bombards the anode target to generate X-ray.

* * * * *